United States Patent
Welsh

(10) Patent No.: US 6,360,886 B1
(45) Date of Patent: Mar. 26, 2002

(54) CAPSULE FOR USE IN PREPARING A DENTAL AMALGAM

(75) Inventor: John H. Welsh, Dearborn Heights, MI (US)

(73) Assignee: Kerr Corporation, Orange, CA (US)

( * ) Notice: Subject to any disclaimer, the term of this patent is extended or adjusted under 35 U.S.C. 154(b) by 0 days.

(21) Appl. No.: 09/524,403

(22) Filed: Mar. 13, 2000

(51) Int. Cl.⁷ .............................................. B65D 81/32

(52) U.S. Cl. ..................... 206/219; 206/63.5

(58) Field of Search .............................. 206/219–222, 206/568, 63.5; 220/792, 796

(56) References Cited

U.S. PATENT DOCUMENTS

| | | |
|---|---|---|
| 85,913 A | 1/1869 | Davis |
| 300,721 A | 6/1884 | Morgan |
| 425,646 A | 4/1890 | Wykoff |
| 525,845 A | 9/1894 | Hobbs |
| 584,270 A | 6/1897 | Palmer |
| 639,595 A | 12/1899 | Mitchell |
| 1,375,479 A | 4/1921 | Van Allen |
| 1,454,836 A | 5/1923 | Slocomb |
| 1,610,908 A | 12/1926 | Westphal |
| 1,858,134 A | 5/1932 | Booth et al. |
| 1,977,580 A | 10/1934 | Grier |
| 2,003,657 A | 6/1935 | Stubblefield |
| 2,135,790 A | 11/1938 | Boeger |
| 2,276,606 A | 3/1942 | Baerenklau |
| 2,487,236 A | 11/1949 | Greenberg |
| 2,527,991 A | 10/1950 | Greenberg |
| 2,549,644 A | 4/1951 | Silverman |
| 2,584,759 A | 2/1952 | Swenson |
| 2,606,708 A | 8/1952 | Irvan |
| 2,614,727 A | 10/1952 | Robinson |
| 2,633,981 A | 4/1953 | Herrick |
| 2,711,840 A | 6/1955 | Gits et al. |
| 2,718,980 A | 9/1955 | Strom |
| 2,722,257 A | 11/1955 | Lockhart |
| 2,768,762 A | 10/1956 | Guinet |
| 2,789,607 A | 4/1957 | Tupper |
| 2,815,057 A | 12/1957 | Tupper |
| 2,886,203 A | 5/1959 | Goll |
| 2,962,187 A | 11/1960 | Morris |
| 3,019,891 A | 2/1962 | Irby |
| 3,023,889 A | 3/1962 | Barr |
| 3,133,663 A | 5/1964 | Schurman et al. |
| 3,139,181 A | 6/1964 | Kobernick |
| 3,151,757 A | 10/1964 | Martin |
| 3,160,303 A | 12/1964 | Healy |
| 3,180,534 A | 4/1965 | Duda et al. |
| 3,258,115 A | 6/1966 | Kath |
| 3,265,202 A | 8/1966 | Cornell |
| 3,285,408 A | 11/1966 | Carnaghi et al. |
| 3,320,993 A | 5/1967 | Motsenbocker |
| 3,323,671 A | 6/1967 | Minarik, Jr. et al. |
| 3,344,914 A | 10/1967 | Bloom et al. |
| 3,353,898 A | 11/1967 | Lamberti |
| 3,393,818 A | 7/1968 | McIntosh |
| 3,398,945 A | 8/1968 | Walpole |
| 3,399,803 A | 9/1968 | Oglevee et al. |
| 3,407,924 A | 10/1968 | Lewis et al. |
| 3,450,302 A | 6/1969 | Braught |
| 3,536,191 A | 10/1970 | Williams |

(List continued on next page.)

Primary Examiner—Jim Foster
(74) Attorney, Agent, or Firm—Wood, Herron & Evans, L.L.P.

(57) ABSTRACT

In one aspect of the invention, a dental amalgam capsule includes a body, a cap, a dental amalgam alloy, and mercury. In further detail, the body has a hollow interior with an open first end which includes an opening surrounded by an end wall. The cap has a hollow interior with an open first end and an interior surface. The interior surface includes an annular recess disposed about a longitudinal axis of the cap, with the annular recess including a sealing surface angled at less than 90 degrees relative to the longitudinal axis. The sealing surface is capable of contacting at least a portion of the end wall, thereby forming a seal with the end wall.

22 Claims, 3 Drawing Sheets

U.S. PATENT DOCUMENTS

| | | | |
|---|---|---|---|
| 3,556,338 A | * 1/1971 | Wilkinson | 220/792 |
| 3,572,413 A | 3/1971 | Livngstone | |
| 3,584,759 A | 6/1971 | Lorincz | |
| 3,595,439 A | 7/1971 | Newby et al. | |
| 3,625,349 A | 12/1971 | Muhlbauer | |
| 3,651,932 A | 3/1972 | Muhlbauer | |
| 3,655,035 A | 4/1972 | Muhlbauer | |
| 3,655,037 A | 4/1972 | Lussier | |
| 3,679,184 A | 7/1972 | Woodham et al. | |
| 3,684,136 A | 8/1972 | Baumann | |
| 3,739,947 A | 6/1973 | Baumann et al. | |
| 3,756,571 A | 9/1973 | Winberg | |
| 3,762,540 A | 10/1973 | Baumann et al. | |
| 3,785,481 A | 1/1974 | Allet-Coche | |
| 3,796,303 A | 3/1974 | Allet-Coche | |
| 3,805,994 A | 4/1974 | Cherry et al. | |
| 3,809,225 A | 5/1974 | Allet-Coche | |
| 3,823,843 A | 7/1974 | Stephens et al. | |
| 3,831,742 A | 8/1974 | Gardella et al. | |
| 3,841,467 A | 10/1974 | Hansen | |
| 3,860,114 A | 1/1975 | Merckardt | |
| 3,881,627 A | 5/1975 | Davolt | |
| 3,917,062 A | 11/1975 | Winters | |
| 3,963,120 A | 6/1976 | Perfect | |
| 4,004,710 A | 1/1977 | Crisci | |
| 4,046,168 A | 9/1977 | Milne | |
| 4,136,775 A | 1/1979 | Zaltsman | |
| 4,180,178 A | 12/1979 | Turner | |
| 4,197,943 A | 4/1980 | Weikel | |
| D255,714 S | 7/1980 | Lancellotti | |
| D258,762 S | 3/1981 | Corrigan et al. | |
| 4,289,252 A | 9/1981 | Helms | |
| 4,306,651 A | 12/1981 | Muhlbauer | |
| 4,341,324 A | 7/1982 | Ramirez | |
| 4,360,119 A | 11/1982 | Olivo | |
| 4,362,242 A | 12/1982 | Cheetham | |
| 4,388,998 A | 6/1983 | Underwood et al. | |
| 4,396,117 A | 8/1983 | Muhlbauer | |
| 4,433,779 A | 2/1984 | Schmid, Jr. et al. | |
| 4,450,957 A | 5/1984 | Cohen | |
| 4,450,958 A | 5/1984 | Prasad | |
| 4,470,505 A | * 9/1984 | Korwin et al. | 206/219 |
| 4,537,303 A | 8/1985 | Muhlbauer | |
| 4,538,741 A | 9/1985 | Jacobs | |
| 4,552,266 A | 11/1985 | Weissenburger | |
| 4,557,376 A | 12/1985 | Probst et al. | |
| 4,632,243 A | 12/1986 | Muhlbauer | |
| 4,632,272 A | 12/1986 | Berenfield et al. | |
| 4,664,257 A | 5/1987 | Nilson | |
| 4,768,669 A | 9/1988 | Kane et al. | |
| 4,773,559 A | 9/1988 | Sasaki et al. | |
| 4,809,871 A | 3/1989 | Angelchik | |
| RE32,927 E | 5/1989 | Taylor et al. | |
| 4,844,308 A | 7/1989 | Porteous | |
| 4,863,017 A | 9/1989 | Vlock | |
| 4,867,305 A | 9/1989 | Schneider | |
| 4,903,855 A | 2/1990 | Ducay et al. | |
| 4,940,135 A | 7/1990 | Hall | |
| 4,941,751 A | 7/1990 | Muhlbauer | |
| 4,960,219 A | 10/1990 | Jordan et al. | |
| 4,966,465 A | 10/1990 | Randklev | |
| 4,968,625 A | 11/1990 | Smith et al. | |
| 4,972,969 A | 11/1990 | Randklev | |
| 5,026,283 A | 6/1991 | Osanai et al. | |
| 5,129,533 A | 7/1992 | Loffler | |
| 5,172,807 A | 12/1992 | Dragan et al. | |
| 5,297,698 A | 3/1994 | Martin | |
| 5,346,083 A | 9/1994 | Song et al. | |
| 5,368,178 A | * 11/1994 | Towns et al. | 220/780 |
| 5,383,558 A | 1/1995 | Wilkinson et al. | |
| 5,392,904 A | 2/1995 | Frick et al. | |
| 5,394,980 A | 3/1995 | Tsai | |
| 5,396,986 A | 3/1995 | Fountain et al. | |
| 5,509,530 A | 4/1996 | Wilson | |
| 5,575,398 A | 11/1996 | Robins, III | |
| 5,577,632 A | 11/1996 | Blanchette et al. | |
| 5,578,491 A | 11/1996 | Kayal et al. | |
| 5,579,935 A | 12/1996 | Atkin et al. | |
| 5,595,907 A | 1/1997 | Kayal et al. | |
| 5,647,501 A | 7/1997 | Helms | |
| 5,660,302 A | 8/1997 | Trout | |
| 5,730,309 A | 3/1998 | Jiradejnunt et al. | |
| 5,758,791 A | 6/1998 | Mangla | |
| 5,769,267 A | 6/1998 | Duynslager et al. | |
| 5,848,692 A | 12/1998 | Thorne et al. | |
| 5,879,634 A | 3/1999 | Ford | |

* cited by examiner

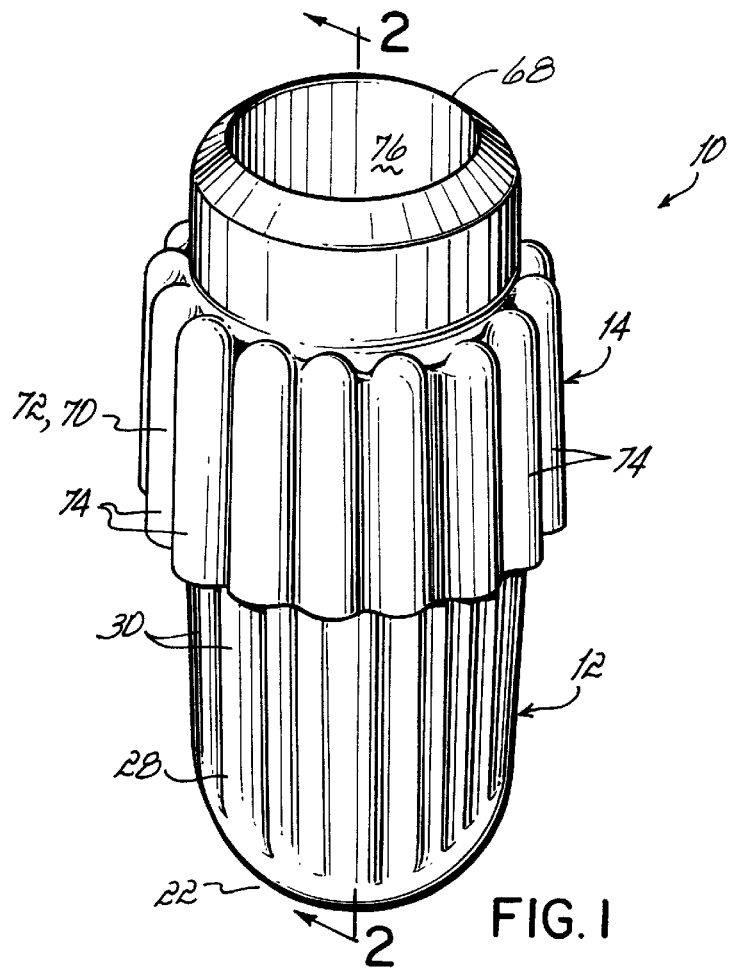
FIG. 1
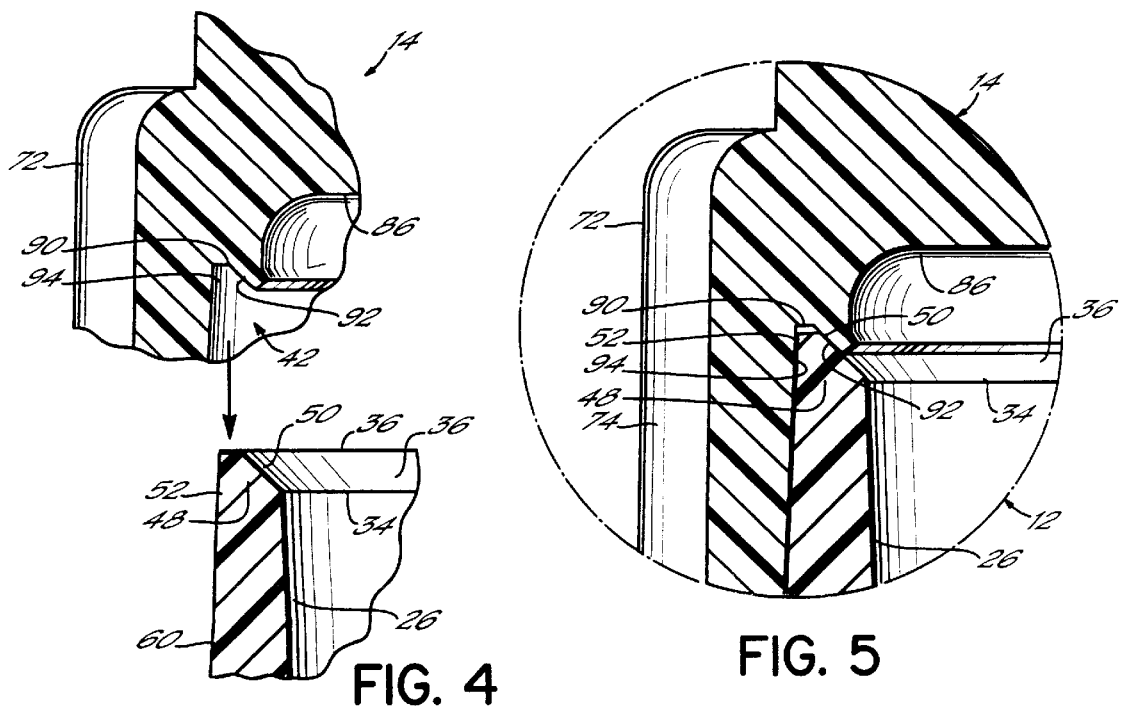
FIG. 4
FIG. 5

CAPSULE FOR USE IN PREPARING A DENTAL AMALGAM

BACKGROUND OF THE INVENTION

1. Field of the Invention

This invention relates to a capsule for use in preparing a dental amalgam, and more particularly, to such a capsule which may be opened to inspect the contents following amalgamation, and, if necessary, securely resealed for further amalgamation.

2. Description of the Related Art

In the field of dentistry, dental professionals use capsule systems in order to prepare dental amalgams for use in filling patients' cavities.

Such capsule systems typically include a body portion and a removable cap portion which combine to form a mixing chamber. Such capsule systems further include an amalgam alloy and mercury, with the mercury being kept separate from the alloy until the dental professional is ready to form the particular amalgam.

In one particular system, a mercury-containing bag or pouch is placed in the chamber body, along with the particular dental amalgam alloy. The chamber body and chamber cap then are welded together, or bonded together using a suitable adhesive or other bonding material. At this point, the particular capsule is placed in an amalgamator, also known as a vibration mixer, which moves the capsule backward and forward at extremely high speeds, generally in a direction which is along the longitudinal axis of the capsule system.

During the amalgamation process, extraordinarily high acceleration forces are exerted on the contents of the capsule. The mercury-containing bag or pouch is designed to rupture or burst due to the reversing forces of the amalgamator.

Once the amalgamator has shaken the capsule system, at a particular frequency for a particular length of time, the dental professional then breaks the seal on the capsule system in order to gain access to the contents of the mixing chamber. Typically, the dental professional breaks the seal by inserting one end of a cylindrical rod into a corresponding cylindrical socket formed on the top of the cap portion. Then, by using the cylindrical rod as a lever, the professional may break the cap portion away from the body portion, and subsequently empty the contents of the mixing chamber into a dental amalgam basin. However, this breaking process is awkward, and may cause accidental spilling of the contents.

Because the body portion and cap portion are welded or bonded together, the risk of premature leakage of mercury is relatively low. However, once the seal between body and cap has been broken, the capsule system may not be placed back in the amalgamator for further mixing, which is a significant drawback.

In further detail, despite the fact that a dental practitioner typically has the ability to set both the speed and time of an amalgamator, visual inspection of the particular dental amalgam typically is required in order to determine whether the amalgam alloy and mercury have been sufficiently mixed. If, after having inspected the contents of the mixing chamber, the dental professional determines that the contents have not been adequately mixed, the dental professional may attempt to further mix the contents by hand, which is not a particularly satisfactory option. This subsequent hand mixing consumes valuable working and handling time, which is a significant drawback given that the particular dental amalgam typically sets within five minutes or less. Yet another equally unpalatable option is to begin the process all over again with a new capsule system. However, this method wastes not only time, but materials as well. Moreover, it still does not eliminate the possibility that the contents of the mixing chamber will require further mixing after the seal of the new capsule has been irreversibly broken, and the contents inspected.

SUMMARY OF THE INVENTION

The invention overcomes the above-mentioned drawbacks by providing a capsule kit having a first capsule member and a second capsule member, in which the first capsule member has a peripheral end wall, and the second capsule member has a corresponding peripheral recess capable of forming a secure, releasable, resealable seal between the first and second capsule members, thereby enabling a dental professional to open the capsule, inspect the contents of the mixing chamber, and, if necessary, reseal the capsule, and place it back in the amalgamator for continued mixing.

In further detail, the first capsule member has an exterior surface, an interior surface, an opening, an interior space and a first end, with the first end having the peripheral end wall. The peripheral end wall includes a width, an inner edge, an outer edge, and a surface which inclines in the direction of the outer edge. The second capsule member has an exterior surface, an interior surface, an opening, an interior space, and a first end, with the interior surface including the peripheral recess which forms the releasable, yet resealable, seal with the peripheral end wall. When the peripheral end wall and the peripheral recess are positioned together to form the seal, the first and second capsule member openings communicate with each other, and the first and second capsule member interior spaces form a mixing chamber.

In another aspect of the invention, the peripheral end wall has a non-contacting portion which is adjacent the inner edge, with the non-contacting portion being in non-contacting relationship with the peripheral recess when the peripheral end wall and the peripheral recess form a seal. In a further aspect, the peripheral recess includes an upper wall having a projecting end which projects toward a central, longitudinal axis of the second capsule member. The distance between the projecting end and the central, longitudinal axis is greater than the distance between the first capsule member end wall inner edge and the central, longitudinal axis, when the peripheral end wall and the peripheral recess form a releasable seal.

In yet another aspect of the invention, the peripheral recess includes an upper wall having a length, with the length of the peripheral end wall being greater than the length of the peripheral recess upper wall. In a further aspect, the peripheral end wall surface which inclines in the direction of the outer edge is substantially planar, and the peripheral recess has an upper wall which also is substantially planar.

In another aspect, the peripheral end wall has a receivable portion which is received by the peripheral recess. The receivable portion includes the peripheral end wall outer edge, an adjacent inner surface, an adjacent outer surface, and a cross-sectional shape having a first angle formed between the adjacent inner surface and the adjacent outer surface. The peripheral recess includes a base, an adjacent upper wall, an adjacent sidewall, and a cross-sectional shape having a second angle formed between the adjacent upper wall and the adjacent sidewall, with the first angle being greater than the second angle. In addition, if desired, the peripheral recess may be made such that it is more flexible than the receivable portion. In this fashion, although the angle of the peripheral recess may be smaller than the angle of the receivable portion, the added flexibility gives the peripheral recess a bit of a spring action, assisting it in biasing against the receivable portion, thereby improving the integrity of the seal.

In yet another aspect of the invention, the first capsule member further includes a peripheral flange which extends from the exterior surface. This peripheral flange has a cross-sectional diameter which increases in the direction of the first end of the first capsule member. If desired, the peripheral flange may have a sidewall which is substantially planar. In addition, if desired, the peripheral flange may have an upper ledge.

In another aspect, the first capsule member includes a peripheral flange extending from the exterior surface, and the second capsule member includes a peripheral, generally V-shaped indentation along the interior surface, with the indentation having a first sidewall. This peripheral, generally V-shaped indentation is capable of releasably engaging the peripheral flange. If desired, the inner diameter of the second capsule member, along the indentation first sidewall, may decrease in the direction of the first end of the second capsule member. Also, if desired, the outer diameter of the peripheral flange may decrease in the direction away from the first end of the first capsule member, with this decrease being at a rate substantially similar to a rate of decrease of the inner diameter of the second capsule member, along the indentation first sidewall, in the direction of the first end of the second capsule member.

The peripheral flange and the peripheral, generally V-shaped indentation discussed briefly above provide a dental practitioner with an easy-to-use, snap-fit securing system. In this fashion, a dental professional knows that the first and second capsule members are releasably secured together by feeling the snap-like aspect of this feature. Also, the peripheral flange and peripheral, generally V-shaped indentation are designed so that a user easily may separate the first capsule member from the second capsule member. In addition, these aspects of the invention are designed to ensure that a tight, releasable, resealable, seal is formed between the peripheral end wall and the peripheral recess of the first capsule member and second capsule member, respectively.

BRIEF DESCRIPTION OF THE DRAWINGS

The accompanying drawings, which are incorporated in, and constitute a part of, this specification, illustrate a version of the invention, and, together with the general description of the invention given above, and the detailed description of the drawings given below, serve to explain the principles of the invention.

FIG. 1 is a perspective view of one version of the capsule in accordance with the principles of the invention;

FIG. 4 is an enlarged, cross-sectional view of a portion of the capsule of FIG. 2; and FIG. 5 is an enlarged, cross-sectional view of a portion of the capsule of FIG. 3.

DETAILED DESCRIPTION OF THE DRAWINGS

Figure 2:
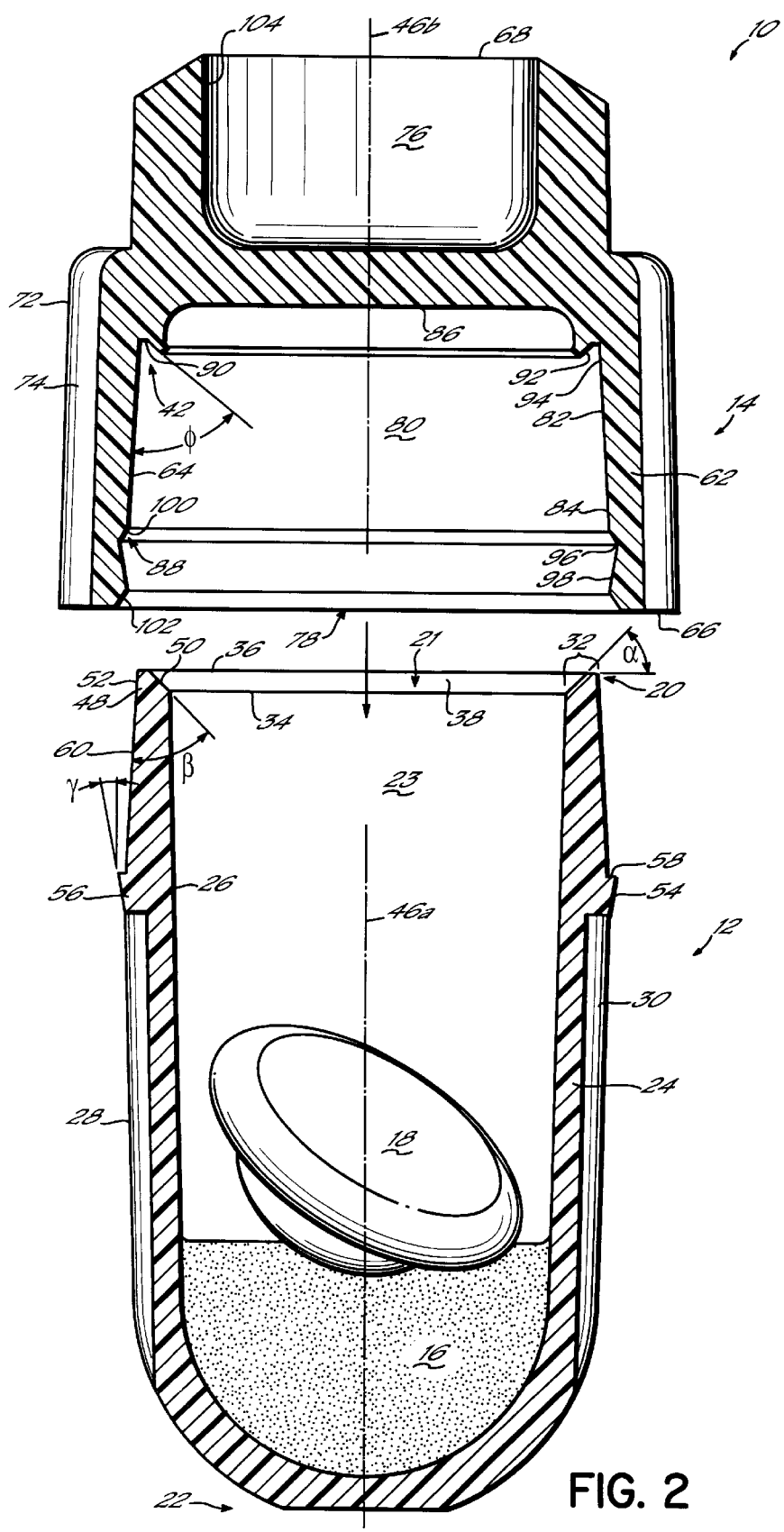
FIG. 2 is a disassembled, cross-sectional view of the capsule of FIG. 1, taken along line 2—2 of FIG. 1.

With references to FIGS. 1–5, a version 10 of the capsule for use in forming a dental amalgam includes a body 12, a cap 14, an amalgam alloy powder 16, and a mercury-containing pillow pack 18, also referred to as a bag, pocket, or pouch.

In further detail, the body 12 is substantially cylindrical in nature, having an open first end 20 and an oppositely positioned, closed second end 22, with a generally cylindrical, circumferential sidewall 24 extending between the first and second ends 20, 22. The first end 20 includes an opening 21 which leads to an interior space 23 and an interior surface 26, with the interior surface 26 being generally smooth. The body 12 further has an exterior surface 28, with both the interior and exterior surfaces 26, 28 being rounded as the body 12 transitions from the sidewall 24 to the second end 22. The exterior surface 28 includes a series of inverted, longitudinal ribs 30 along much of the sidewall 24 (see FIG. 1), which assists a user in grasping the body 12, separating the body 12 from the cap 14, and, if needed, resealing the body 12 and the cap 14.

The first end 20 of the body 12 includes an end wall 32 having an inner edge 34, an outer edge 36, and a peripheral surface in the form of an inclined or tapered surface 38 extending between the inner and outer edges 34, 36, with the inclined surface 38 extending radially upward and outward relative to a central longitudinal axis of the body 12. While not required, advantageously, this surface 38 may be in the form of a truncated cone. In addition, the surface 38 may incline at any suitable angle $\alpha$, with 45° being an example of one such suitable angle.

In addition, the body 12 has a circumferential flange 54 which extends radially outward from the exterior surface 28 of the body sidewall 24. In further detail, this flange 54 has a truncated conical surface 56 which slopes outwardly and upwardly (FIG. 2). If desired, the conical surface 56 may be angled at about 10° relative to a longitudinal axis of the body 12, as shown by angle $\gamma$ (FIG. 2). As shown, the circumferential flange 54 also includes an upper ledge or shoulder 58. However, as will be understood by one of ordinary skill upon reading this detailed description, the circumferential flange may be of any suitable size or shape, as long as it interacts with a cooperating internal circumferential groove formed in the cap to provide a secure, yet releasable, attachment of the body to the cap. Advantageously, the construction and arrangement of the flange 54 is such that it cooperates with the internal groove in the cap to provide a "snap fit" releasable engagement between the body and the cap. Moreover, the shape and sizing of the flange and corresponding feature or features (to be discussed in detail below) of the cap are such that the body and the cap may be snapped together easily by hand, and also may be separated easily by hand.

The exterior surface 28 of the body 12, as shown, further includes a sidewall portion 60 which extends from the shoulder 58 to the first end 20. This portion 60 forms a frictional fit with a corresponding sidewall portion 62 (discussed in detail below) on the interior surface 64 of the cap 14. While not required, the portion 60, as shown, is substantially in the form of a truncated cone, and includes a draft, with the taper extending in the direction of the first end 20. If a draft, or taper, is provided, any suitable angle may be used. For example, if desired, the sidewall portion 60 may have a draft of about 3° relative to the longitudinal axis of the body 12.

If desired, other surfaces of the body 12 may be provided with any suitable draft. For example, the sidewall interior surface 26 may have a 1° draft tapering toward the body second end 22. Likewise, the portion of the exterior surface 28 of the sidewall 24 which extends from the circumferential flange 54 toward the second end 22 may have a 1° draft tapering toward the second end 22 of the body 12.

Figure 3:
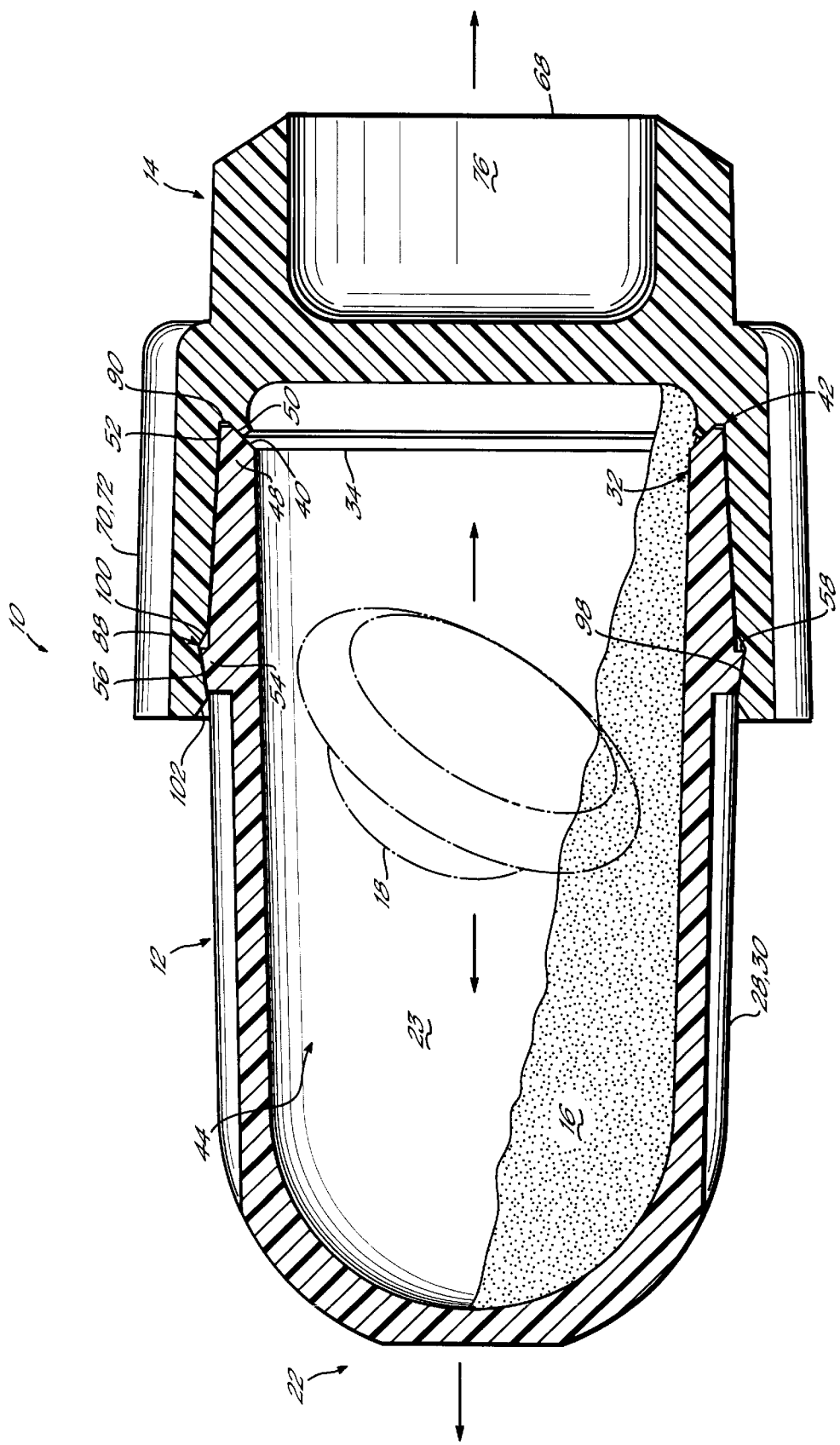
FIG. 3 is a cross-sectional view of the capsule of FIG. 1.

The cap 14 of the capsule 10 shown in FIGS. 1–3 has a first end 66 and an oppositely positioned, second end 68, with a generally circumferential sidewall 70 connecting the first and second ends 66, 68. In further detail, the cap 14 has an exterior surface 72 with a series of longitudinal ribs 74 extending approximately two-thirds of the way along the length of the sidewall 70, from the cap first end 66 toward the second end 68. The second end 68 also has a cylindrical recess 76 which, if desired, may be used to assist a dental professional in positioning the capsule 10 (see FIG. 3) in a vibratory mixer or amalgamator. The first end 66 has an opening 78 which leads to an interior space 80 and an interior surface 82, with the interior surface 82 being generally smooth. The interior surface 82 has several surface features, including, for example, a slightly tapered, generally cylindrical interior sidewall surface 84, an end wall 86, a circumferential recess 42 near the end wall 86, and a circumferential groove 88, near the cap first end 66. The cap 14 also has a central, longitudinal axis 46b (see FIG. 2) which, as shown, is coaxial with the central longitudinal axis 46a of the body 12.

The recess 42 is extremely valuable in that it provides, in conjunction with the body end wall 32, a seal which is not only secure, but is also readily releasable. Moreover, the cap 14 and the body 12 of the capsule easily may be separated by a dental practitioner as many times as are needed to inspect the contents of the capsule, with the recess 42 and end wall 32 features cooperating to form a secure seal each time the practitioner subsequently reattaches the cap 14 and the body 12.

The circumferential recess 42, itself, includes a base 90, an adjacent upper wall surface or sealing surface 92, and an adjacent sidewall surface 94, with the recess 42 having a cross-sectional shape, when viewed longitudinally, in which an angle φ, also referred to as a second angle, is formed between the sealing surface wall 92 and the adjacent sidewall surface 94 (see FIG. 2). Any suitable angle may be used, with 35° being one such angle. The recess 42, including the base 90, the sealing surface 92, and the adjacent sidewall surface 94, may have any size, configuration, and/or shape capable of suitably cooperating with the end wall 32 of the body 12 to form an effective, releasable seal. As shown, both the sealing surface 92 and the adjacent sidewall surface 94 are substantially in the form of truncated cones, which correspond generally with the surfaces of the end wall 32.

If desired, the angle φ of the circumferential recess 42 may be smaller than the angle β of the male sealing lip section 48 of the end wall 32. Such a relatively smaller angle φ is particularly advantageous when the material (or materials) which forms the recess 42 is more flexible than the material (or materials) which forms the lip section 48 of the end wall 32. Such features form a seal which is highly effective. In this situation, the recess 42, and especially the sealing surface 92, tends to have a flexing, or spring-like, action. Therefore, as the cap 14 is attached to the body 12, the recess 42 flexes to conform to the shape of the lip section 48 of the end wall 32. Furthermore, because the second angle is smaller than the first angle, the recess 42 tends to bias against the lip section 48.

As shown, the cap 14 further includes an interior circumferential groove 88, which is generally V-shaped. This groove 88 is capable of releasably frictionally engaging the circumferential flange 54 (described in detail above) of the body 12, in order to form an easy-to-use "snap fit" attachment mechanism.

In the version of the cap shown in FIGS. 2 and 3, the groove 88, when viewed in longitudinal cross-section, has a V-shape defined by truncated conical surfaces 98, 100 which intersect in a circular line 96. The conical surfaces 98, 100 are differently angled. As shown, the inner diameter of the conical surface 98 decreases in the direction of the first end 66 of the cap 14, whereas the inner diameter of the conical surface 100 increases in the direction of the first end 66 of the cap 14. In addition, the rate of decrease of the inner diameter of the cap 14 along the conical surface 98 is substantially similar to the rate of decrease of the outer diameter of the body circumferential flange 54 in the direction away from the first end 20 of the body 12. Stated somewhat differently, the taper of the conical surface 98 corresponds generally with the taper of the flange truncated conical surface 56. As will be appreciated by one of ordinary skill in the art, any suitable taper may be used. For example, if desired, an angle of about 10° relative to a cap longitudinal axis, such as the central, longitudinal axis 46b, may be used to advantage. Also by way of example, the conical surface 100 may have an angle of about 26° relative to a cap longitudinal axis, such as the central, longitudinal axis 46b.

As noted in conjunction with the circumferential flange 54, the interior groove 88 may have any size, shape, and/or configuration which provides for a suitable, secure, easily releasable, attachment mechanism. For example, in another version of the cap (not shown), one conical surface is substantially perpendicular to the longitudinal axis 46b, in which case, the interior groove would have a cross-sectional profile much like a "7" (or the mirror image of a 7). Also, if desired, the location of the groove and the flange may be reversed. For example, the groove may be positioned on the body, and the flange may be located on the cap.

The cap 14 further includes a corresponding tapered sidewall surface portion 62 along the interior surface 64 of the cap sidewall 70, with the portion 62 forming a frictional fit with the sidewall surface portion 60 of the body 12. In further detail, the corresponding sidewall surface portion 62 extends from the annular recess 42 to the interior groove 88. Although not required, the surface portion 62 typically has a draft, which, if desired, corresponds to the draft of the body sidewall surface portion 60. For example, if the body sidewall surface portion 60 has a draft of about 3°, then the corresponding sidewall surface portion 62 may have a draft of about 3°. Also, if desired, the inside diameter of the cap 14, along the corresponding sidewall surface portion 62, may be slightly less than the outside diameter of the body 12, along the sidewall surface portion 60, thereby assisting in forming a frictional fit between the two surface portions 60, 62.

The interior surface 64 of the cap sidewall 70 which is adjacent the first end 66 has a surface portion 102 which tapers radially outward, in the direction of the first end 66, thereby providing the opening 78 with a slightly larger inner diameter than it would have if there were no taper. This feature functions as a chamber to assist in manually guiding the cap 14 onto the body 12. If desired, this surface portion 102 may taper at an angle of, for example, about 30°, relative to the cap central, longitudinal axis 46b. The exterior surface 72 of the cap sidewall 70 may be provided with a draft of about 1°. Likewise, the cylindrical recess sidewall 104 may be provided with a similar draft.

The end wall surface 38 has a non-sealing portion 40 (see FIG. 3) which is adjacent the inner edge 34, with the non-sealing portion 40 being in non-sealing relationship with the annular recess 42 of the cap 14, when the end wall 32 and the annular recess 42 form a releasable seal (see FIG. 3). This non-sealing portion 40 helps direct capsule contents toward the central, longitudinal axis 46a, 46b of the capsule 10, and away from the seal formed between the body 12 and cap 14, when the contents move generally away from the cap end wall 86 and toward the body bottom end 22, thereby assisting in keeping the contents of the capsule mixing chamber 44 out of the seal. The mixing chamber 44 includes the interior surfaces of the body 12 and cap 14 which are exposed when the body 12 and cap 14 are secured together, as shown in FIG. 3, as well as the interior space defined by such interior surfaces.

The peripheral end wall 32 of the body 12 also has a male sealing lip section 48 (FIG. 3) which is received by the annular recess 42 of the cap 14. This lip section 48 includes the peripheral end wall outer edge 36, an adjacent inner surface 50, and an adjacent outer surface 52, which, when viewed in longitudinal cross-section, forms a shape having an angle β, also referred to as a first angle, formed between the adjacent inner surface 50 and the adjacent outer surface 52 (see FIGS. 2 and 3).

As will be appreciated, in providing a releasable, refastenable snap-fit mechanism, the body 12 and the cap 14 may have any combination of cooperating features. For example, the body 12 may have one or more projections, other than a circumferential flange 54, which cooperate with the cap 14. Also, the flange 54, or another surface projection or projections, may be positioned on the cap, for example, along the cap interior surface. In such a version, the body 12 may have one or more indentations or other surface features for cooperating with such a projection or projections on the cap 14; and, if desired, the body may be free of surface projections.

The capsule body and cap may be made using any suitable manufacturing process, as will be apparent to one of ordinary skill in the art upon reading this detailed description. For example, if desired, conventional thermoplastic injection molding may be used. With regard to materials, and as mentioned briefly above, any suitable materials may be used. However, in order to take maximum advantage of the sealing and snap-fit aspects of the invention, it is advantageous to use materials for the cap which are more flexible than the materials used for the body. For example, if desired, the cap may be made of Equistar NA 860 polyethylene, available from Equistar Chemical, LP, Cincinnati, Ohio, and the body may be made of Nova high-impact polystyrene no. 331, available from Nova Chemical of Calgary, Alberta, Canada.

Once the capsule body 12 and cap 14 of the present invention have been manufactured, they are ready for use. At this point, a dental amalgam alloy and any suitable mercury-containing device may be put into the capsule body 12, and the cap 14 and body may be snapped together, thereby forming a releasably sealed, resealable capsule having a mixing chamber 44 containing both alloy and isolated mercury.

As will be appreciated by those of ordinary skill, any suitable dental amalgam alloy and mercury-containing device may be used. For example, if desired, an amalgam alloy such as Tytin FC™, Tytin®, Contour™, or Sybraloy® amalgam alloy, available from the Kerr Corporation, a subsidiary of Sybron Dental Specialities, Inc., Orange, Calif., may be used. In addition, if desired, the mercury-containing device may be a pillow pack, such as a pillow pack 18 available from DMG Hamburg, Hamburg, Germany. Exemplary DMG pillow-packs are available as DMG part nos. 509114, 509136, 509137, 509138, 509139, 509141, 509142, 509143, 509144, 509145, 509142, 509146, 509147.

In using a capsule made according to the principles of the invention, a dental practitioner may form the desired dental amalgam using any suitable amalgamator or vibration mixer. For example, if desired, the OptiMix™ amalgamator, available from the Kerr Corporation, a subsidiary of Sybron Dental Specialities, Inc., Orange, Calif., may be used.

While the present invention has been illustrated by description of a particular version shown in the drawings, and while the illustrative version has been described in considerable detail, the inventor does not intend to restrict, or in any way limit the scope of the appended claims to such detail. Additional advantages and modifications will readily appear to those of ordinary skill in the art upon reading this detailed description. Therefore, the invention, in its broader aspects, is not limited to the specific details, representative apparatus and methods, and illustrative examples shown and described. Accordingly, departures may be made from such details without departing from the spirit or scope of the inventor's general inventive concept.

What is claimed is:

1. A capsule for holding a dental amalgam, comprising:
a body having a hollow interior with an open first end which includes an opening surrounded by an end wall, the end wall having a male sealing lip section and a radially upwardly and outwardly extending inclined surface which includes a non-sealing portion; and
a cap having an end wall and a hollow interior with an open first end and a concave interior surface, the interior surface including an annular recess disposed about a longitudinal axis of the cap, the annular recess including a truncated conical sealing surface inclined at an angle of less than 90 degrees relative to the longitudinal axis of the cap,
the male sealing lip section and the sealing surface of the annular recess capable of forming a seal when positioned in a contacting relationship so that the dental amalgam is enclosed within the hollow interiors of the body and the cap, the non-sealing portion located radially inward of the sealing surface of the annular recess when the seal is formed,
the non-sealing portion of the inclined surface deflecting the dental amalgam in a direction away from the seal formed between the male sealing lip section and the sealing surface of the annular recess, thereby inhibiting the dental amalgam moving between the end wall of the cap and the body from penetrating the seal when the sealed amalgam capsule is shaken.

2. The capsule of claim 1 wherein the length of male sealing lip section is greater than the length of the sealing surface of the annular recess.

3. The capsule of claim 1 wherein the male sealing lip section is substantially in the form of a truncated cone.

4. The capsule of claim 3 wherein the sealing surface of the annular recess has an included angle substantially equal to the included angle of the male sealing lip section for providing an effective seal therewith.

5. The capsule of claim 1 wherein the end wall has a sidewall surface adjacent to the male sealing lip section, the end wall having an angle defined by the juncture of the male sealing lip section and the adjacent sidewall surface when viewed in cross-section, the angle of the male sealing lip section being greater than an interior angle of the annular recess to create an effective releasable seal therebetween by biasing the recess against the male sealing lip section.

6. The capsule of claim 5 wherein at least a portion of the cap surrounding the annular recess is more flexible than the male sealing lip section to promote an effective releasable seal therebetween by resiliently conforming the annular recess to the shape of the male sealing lip section.

7. The capsule of claim 1 in combination with a dental amalgam alloy.

8. The capsule of claim 1 in combination with mercury.

9. The capsule of claim 8 in combination with a dental amalgam alloy powder.

10. The capsule of claim 1 wherein the sealing surface of the annular recess extends downwardly and inwardly for engaging the male sealing lip section.

11. The capsule of claim 5 wherein the interior angle of the annular recess is 35 degrees and the angle of the male sealing lip section is greater than 35 degrees.

12. The capsule of claim 1 wherein the exterior surface of the body includes an outwardly-projecting circumferential flange, and the interior surface of the end wall of the cap includes a circumferential groove, the groove positioned and configured receive the flange in a releasable frictional engagement.

13. The capsule of claim 12 wherein the frictional engagement between the groove and flange ensures a tight seal between the male sealing lip of the body against the sealing surface of the cap.

14. The capsule of claim 12 wherein the outer diameter of the body decreases from the flange toward the open first end and the inner diameter of the cap increases from the end wall to the groove, the difference in the inner and the outer diameters providing a frictional fit between the exterior surface of the body and the interior surface of the cap when the body and cap are engaged.

15. The capsule of claim 14 wherein the decrease in the outer diameter of the body creates a decreasing taper of about three degrees and the increase in the inner diameter of the body creates an increasing taper of about three degrees.

16. The capsule of claim 12 wherein the groove includes an inwardly-facing first truncated conical surface and the flange includes an outwardly-facing truncated conical surface, the tapers of the conical surfaces being complementary to provide a close contacting engagement.

17. The capsule of claim 1 wherein:
the body has a longitudinal axis; and
the male sealing lip section and the non-sealing portion are coextensive and have substantially the same angle of inclination relative to the longitudinal axis of the body.

18. A method of using a dental amalgam capsule, the dental amalgam capsule including:
a body having a hollow interior with an open first end which includes an opening surrounded by an end wall, the end wall having a male sealing lip section and a radially upwardly and outwardly extending inclined surface which includes a non-sealing portion; and a cap having an end wall and a hollow interior with an open first end and an interior surface, the interior surface including an annular recess disposed about a longitudinal axis of the cap, the annular recess including a sealing surface angled at less than 90 degrees relative to the longitudinal axis of the cap, and the male sealing lip section and the sealing surface of the annular recess capable of forming a seal when positioned in a contacting relationship, the method comprising the steps of:

placing an alloy powder in the hollow interior of one or the other of the body and the cap while the body and the cap are disengaged;

placing a rupturable package containing mercury in the hollow interior of one or the other of the body and the cap while the body and the cap are disengaged;

engaging the body and the cap so as to place the male sealing lip section in sealing contact with the sealing surface of the annular recess, thereby forming a sealed dental amalgam capsule, with the alloy powder and the rupturable package inside the sealed dental amalgam capsule;

placing the sealed dental amalgam capsule in an amalgamator and shaking the sealed dental amalgam capsule sufficient to rupture the rupturable package, thereby creating a ruptured package and released mercury and forming a mixture of at least some of the alloy powder and some of the released mercury while the capsule remains sealed, wherein a portion of the alloy powder and a portion of the released mercury moving from the end wall of the cap toward the body strike the non-sealing portion of the radially upwardly and outwardly extending inclined surface of the end wall and are deflected away from the seal formed between the male sealing lip section and the sealing surface of the annular recess, thereby inhibiting the portion of the alloy powder and the portion of the released mercury from penetrating the seal; and removing the sealed dental amalgam capsule from the amalgamator, and while removed therefrom, disengaging the body and the cap, thereby facilitating access to the mixture.

19. The method of claim 18 further comprising the steps of:

re-engaging the cap and the body so as to again place the male sealing lip section in sealing contact with the sealing surface of the annular recess, thereby forming a resealed dental amalgam capsule with at least a portion of the mixture inside the resealed capsule;

placing the resealed dental amalgam capsule in the amalgamator and shaking the resealed dental amalgam capsule, thereby further mixing the portion of the mixture inside the resealed dental amalgam capsule; and removing the resealed dental amalgam capsule from the amalgamator, and while removed therefrom, disengaging the body and the cap, thereby facilitating access to the portion of the mixture.

20. The method of claim 19 further including the step of removing the portion of the mixture after removing the resealed dental amalgam capsule from the amalgamator and disengaging the body and the cap, thereby having a removed portion, and inserting at least a part of the removed portion into a prepared cavity in a patient's tooth.

21. The method of claim 19 further including the step of removing the portion of the mixture after removing the resealed dental amalgam capsule from the amalgamator and disengaging the body and the cap, thereby having a removed portion, and inserting at least a part of the removed portion into a prepared cavity in a patient's tooth.

22. A method of using a dental amalgam capsule, the dental amalgam capsule including:

a body having a hollow interior with an open first end which includes an opening surrounded by an end wall, the end wall having a male sealing lip section and a radially upwardly and outwardly extending inclined surface which includes a non-sealing portion; and a cap having an end wall and a hollow interior with an open first end and an interior surface, the interior surface including an annular recess disposed about a longitudinal axis of the cap, with the annular recess including a sealing surface angled at less than 90 degrees relative to the longitudinal axis of the cap, the method comprising the steps of:

contacting the male sealing lip section and the sealing surface of the annular recess to form a seal therebetween for enclosing the dental amalgam within the hollow interiors of the body and the cap;

shaking the sealed dental amalgam capsule to mix the dental amalgam contained therein; and deflecting dental amalgam moving between the end wall of the cap and the body away from the seal formed between the male sealing lip section and the sealing surface, the deflection provided by the non-sealing portion of the inclined surface, thereby inhibiting the dental amalgam from penetrating the seal when the sealed amalgam capsule is shaken.

\* \* \* \* \*

UNITED STATES PATENT AND TRADEMARK OFFICE
CERTIFICATE OF CORRECTION

PATENT NO.     : 6,360,886 B1
DATED          : March 26, 2002
INVENTOR(S)    : John H. Welsh It is certified that error appears in the above-identified patent and that said Letters Patent is hereby corrected as shown below:

Column 9,
Line 23, reads "configured receive" and should read -- configured to receive --.

Signed and Sealed this

Sixteenth Day of July, 2002

Attest:

Attesting Officer

JAMES E. ROGAN
Director of the United States Patent and Trademark Office